US00PP08621P

United States Patent [19]

Olsen et al.

[11] Patent Number: Plant 8,621

[45] Date of Patent: Mar. 1, 1994

[54] APPLE TREE—OBROGALA CULTIVAR

[75] Inventors: Richard R. Olsen; Larry M. Olsen, both of Prosser, Wash.

[73] Assignee: Stark Brothers Nurseries and Orchards, Louisiana, Mo.

[21] Appl. No.: 879,215

[22] Filed: May 6, 1992

[51] Int. Cl.[5] ..... A01H 5/00

[52] U.S. Cl. ..... Plt./34.1

[58] Field of Search ..... Plt. 34.1

*Primary Examiner*—James R. Feyrer
*Assistant Examiner*—Erich E. Veitenheimer
*Attorney, Agent, or Firm*—Burns, Doane, Swecker & Mathis

[57] ABSTRACT

A new and distinct variety of Gala-type apple tree is provided which originated as a whole tree mutation of the Tenroy cultivar (U.S. Plant Pat. No. 4,121). The fruit of the new variety can be distinguished by its attractive solid Nopal Red blush ground color which forms over approximately 90 to 100 percent of the fruit surface with hints of indeterminate striping or less-colored fruit. The coloration of the fruit of the new cultivar develops earlier than that of Tenroy. The fruit of the new variety tends to be more conical in configuration than that of Tenroy, matures for harvest earlier than that of Tenroy, and is excellent in texture and flavor. Also, the bark lenticels of the new cultivar tend to be less flattened in configuration than those of Tenroy (as illustrated).

3 Drawing Sheets

SUMMARY OF THE INVENTION

The new variety originated as a whole tree mutation of the Tenroy cultivar (U.S. Plant Pat. No. 4,121). The Tenroy cultivar is a mutation of the Kidd's D-8 cultivar (U.S. Plant Pat. No. 3,637). The mutation of the present invention was discovered by us during August, 1988, as a three year-old tree growing in solid block of Tenroy trees located at Ranch No. 11 of Olsen Bros. Ranch, Inc., Prosser, Wash. 99350, U.S.A. The causation of the mutation is unknown.

The fruit coloration of the new variety was noted to be particularly distinctive and to be readily distinguishible from that of the Tenroy cultivar. For this reason the new cultivar has been preserved and studied. It has been confirmed that the new cultivar possesses a novel combination of characteristics, and constitutes a commercially important addition to the previously available cultivars of Gala-type apple trees. Had we not discovered and preserved the original tree of the new cultivar it would have been lost to mankind.

It has been found that the new Gala-type apple cultivar of the present invention possesses the following combination of characteristics:

(a) forms attractive fruit of excellent flavor and texture having a Nopal Red blush over approximately 90 to 100 percent of the skin with hints of striping on less colored fruit and greater red coloration than the Tenroy cultivar,
(b) begins color development on the fruit skin approximately 10 days earlier than the Tenroy culivar,
(c) forms fruit which matures for harvest approximately 2 to 4 days earlier than the Tenroy cultivar,
(d) forms fruit which tends to be somewhat more conical than that of the Tenroy cultivar, and
(e) forms lenticels which tend to be irregularly rounded and in the substantial absence of lenticels which are elongated as commonly exhibited by the Tenroy cultivar.

The fruit of the new cultivar begins its color development as a stripe; however, stripes on approximately 90 to 100 percent of the fruit surface fill to the attractive solid Nopal Red coloration. Colorimetric evaluation of typical fruit samples of the new cultivar has confirmed that it exhibits less white and yellow and greater red coloration than the Tenroy cultivar.

The fruit of the new cultivar exhibits an excellent texture and flavor and matures for harvest earlier than the Tenroy cultivar as previously indicated. Such earlier fruit maturity for trees grown at the same location in the state of Washington has been confirmed by the following starch-iodine readings obtained while using the Washington State Apple Maturity Program Scale (Bartram) of 1 to 6:

| Date | TENROY Cultivar | OBROGALA Cultivar |
|---|---|---|
| August 15, 1990 | 1.2 | 2.0 |
| August 23, 1990 | 1.5 | 2.3 |
| August 27, 1990 | 3.2 | 4.2. |

The new cultivar of the present invention can be distinguished from trees of other Gala-type apple trees, such as the Kidd's D-8 cultivar (U.S. Plant Pat. No. 3,637), the Scarlet Gala cultivar (U.S. Plant Pat. No. 6,172), the Galaxy cultivar (U.S. Plant Pat. No. 6,955), and Tresco Spur Red Gala No. 42 cultivar (U.S. Plant Pat. No. 7,396) in view of the combination of characteristics discussed herein.

More specifically, the new cultivar can be distinguished from the Galaxy cultivar in the areas identified hereafter.

(1) The new variety commonly exhibits more overall red coloration on the ripened fruit that extends over approximately 90 to 100 percent of the skin while the red coloration of the ripened fruit of the Galaxy cultivar commonly extends over approximately 80 to 100 percent of the skin.

(2) The red fruit coloration present on the ripened fruit of the new variety commonly is darker than that found on the ripened fruit of the Galaxy cultivar. When ripened fruit of the new variety is inspected, the deep red undercolor with darker stripes commonly is Red Group 46A to 46B ranging to Red Group 53A to 53B in accordance with the R.H.S. Colour Chart of The Royal Horticultural Society. This can be compared to an undercolor of Red Group 42A to 42B ranging to Red Group 45A to 45C for the Galaxy cultivar.

(3) The pattern of red coloring on ripened fruit of the new variety is significantly different. For instance, the new variety commonly exhibits on the ripened fruit a slightly splashed and somewhat blushed undercolor with indistinct striping. On the contrary the ripened fruit of the Galaxy cultivar commonly exhibits a markedly splashed undercolor with more distinct stripes. The overall appearance of the Galaxy cultivar is a brighter red than that exhibited by the new cultivar.

(4) The fruit of the new variety matures significantly earlier than that of the Tenroy cultivar as previously discussed. No maturity difference was observed between the Tenroy and Galaxy cultivars during 1922. Accordingly, it is anticipated that the fruit of the new cultivar will mature significantly earlier than that of the Galaxy cultivar.

(5) The fruit shape of new cultivar tends to be longer and more conic than that of the other Gala-type cultivars, including that of the Galaxy cultivar. The calyx basin tends to be narrower with more distinct points being observed at the base of the fruit. The ratio of the axial to transverse diameters of the fruit of the new cultivar commonly is approximately 0.8 to 0.95:1, while that of the other Gala-type cultivars, including the Galaxy cultivar, tends to be approximately 0.7 to 0.85:1.

It has been found that the characteristics of the new cultivar or apple tree of the present invention are firmly fixed. More specifically, asexual reproduction carried out by budding and grafting at Prosser, Wash., and at Louisiana, Mo., has confirmed that the characteristics are reliably transmitted through succeeding propagations.

The new cultivar has been named the Obrogala cultivar and is being marketed under the UltraRed trademark by Stark Brothers Nurseries and Orchards Company.

BRIEF DESCRIPTION OF THE PHOTOGRAPHS

The accompanying photographs show typical specimens of the new cultivars as depicted in color as nearly true as it is reasonably possible to make the same in color illustrations of this character. All trees were grown at Prosser, Wash., with the exception of the Scarlet Gala cultivar which is shown for comparative purposes and was grown in Kentucky.

FIG. 1 illustrates during 1988 specimens of typical fruit at maturity of the new Obrogala cultivar (center) and that of two other cultivars (on each side) which are presented for comparative purposes. Mature fruit of the Scarlet Gala cultivar is shown on the left and mature fruit of the Tenroy cultivar is shown on the right. Differences in fruit coloring and configuration are apparent.

FIG. 2 illustrates during 1990 typical fruit specimens when commercially ripe of the Obrogala cultivar on the left and of the Tenroy cultivar on the right. The portion of the fruit with the most red coloration is facing the camera in each instance. Differences in fruit coloring are apparent.

Figure 1:
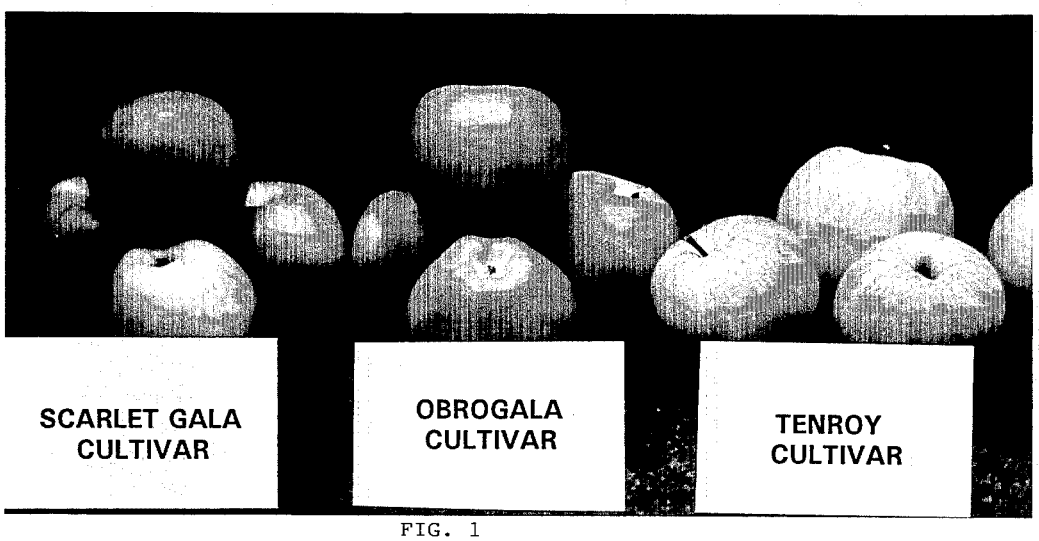
Figure 2:
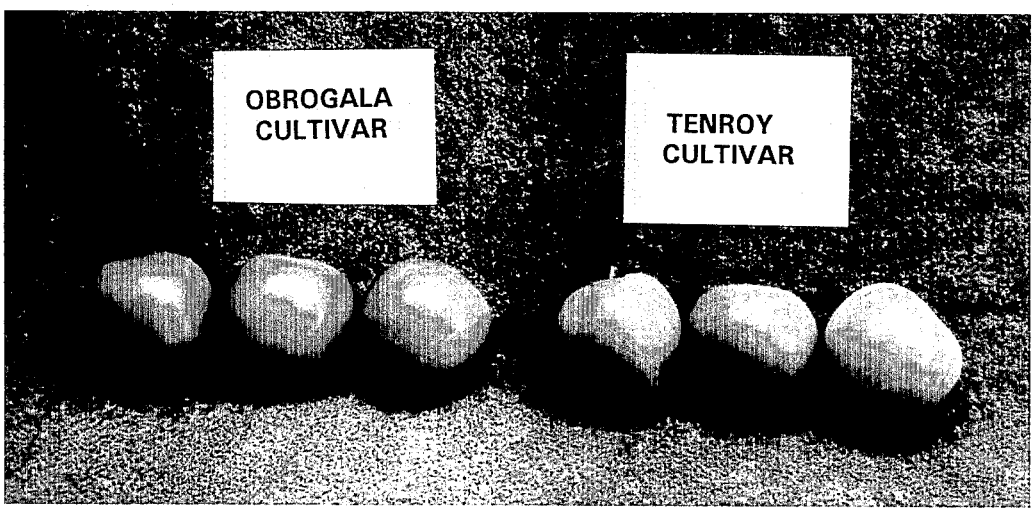
Figure 3:
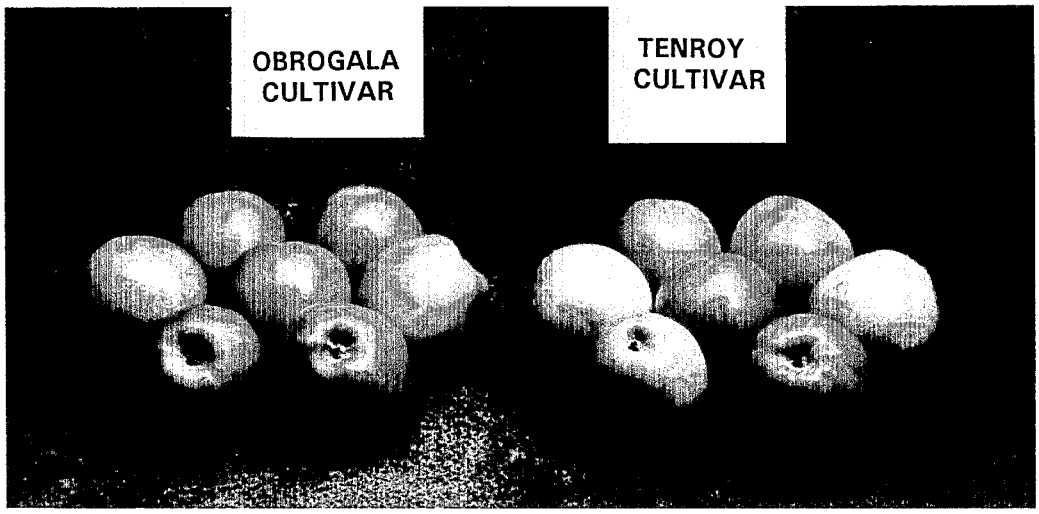
FIG. 3 illustrates during 1990 a random array of typical fruit specimens when commercially ripe of the new Obrogala cultivar on the left and of the Tenroy cultivar on the right. Differences in fruit coloration are apparent.
Figure 4:
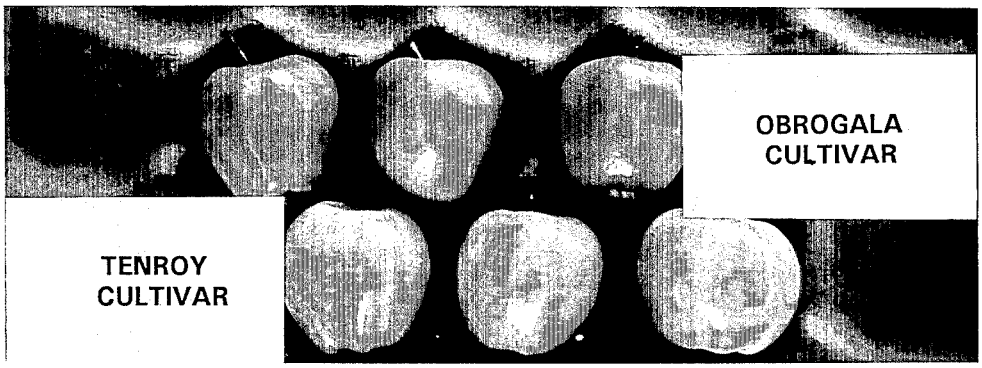
FIG. 4 illustrates on Aug. 30, 1991 on the top row three typical fruits of the new Obrogala cultivar, and on the bottom row three typical fruits of the Tenroy cultivar. The fruit of the Obrogala cultivar is more uniformly blushed while that of the Tenroy cultivar exhibits considerably more striping.
Figure 5:
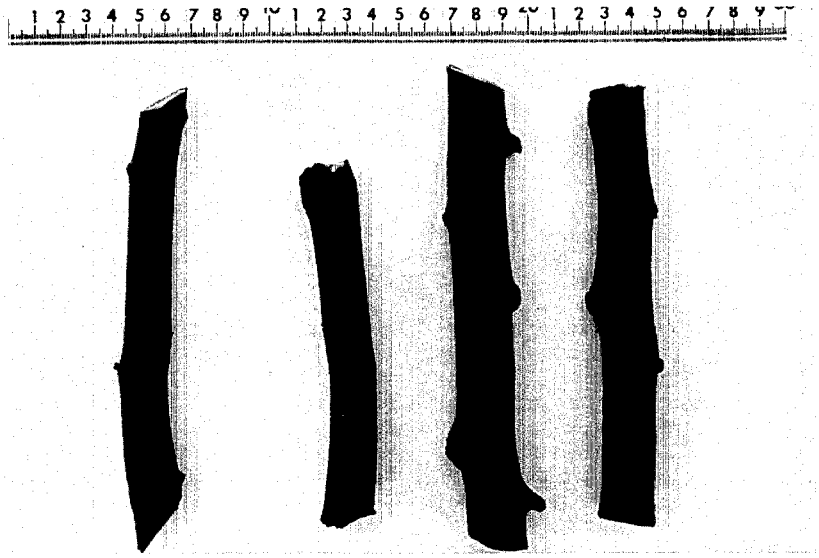

FIG. 5 illustrates during January 1992 portions of typical branches of the Obrogala cultivar (two outside segments) and of the Tenroy cultivar (two inside segments). The branches were of substantially the same age in each instance. It will be noted that the lenticels of the Obrogala cultivar tend to be more rounded in the substantial absence of those which are elongated, while the lenticels of the Tenroy cultivar tend to include in a substantial quantity those which are somewhat elongated and horizontally disposed across the axis of the branch.

DETAILED DESCRIPTION

The following is a detailed description of our new variety. The specimens described were grown at Processer, Wash., U.S.A. Reference is made to Ridgway's Color Standards and Nomenclature except where general color terms are used which are to be accorded their usual and customary significance.

Tree: Medium small; vigorous; spreading; low; round-topped; medium-slow growing; hardy; productive; and regular bearing.

*Bark.*—The lenticels are numerous medium-large and tend to be irregularly rounded in configuration in the substantial absence of lenticels which are elongated or flattened and aligned substantially perpendicular to the branch as commonly exhibited by the Tenroy cultivar. See FIG. 5.

*Trunk.*—Medium smooth.

*Branches.*—Medium thick; smooth; much branching; Light Mouse Gray Plate L1, Color No. 15''''', tone b.

*Leaves.*—Length, approximately 3½ to 4 inches; width, approximately 1¾ to 2 inches; medium-large; medium-wide; more oval in shape than those of the Tenroy cultivar; abruptly pointed; Empire Green Plate XXX11, Color No. 33'', tone b.

*Leaf margin.*—Crenate; finely serrate.

Flowers: During 1991, the first bloom appeared on April 21st, and full bloom appeared on April 23rd. The size is medium; and the color is white with pink fading to white on the under side.

Fruit:

*Size.*—Uniform; the axial diameter is approximately 2¾ inches and the transverse diameter is approximnately 2¾ inches.

*Form.*—Generally globose and approaching a conical configuration. Tends to be somewhat more conical than the Tenroy cultivar.

*Cavity.*—Symmetrical and abrupt at base; apex is acuminate; the depth is approximately ⅞ inch; the breadth is approximately ½ inch; and markings are absent.

*Basin.*—Symmetrical; rounded; wide; undulate; the depth is approximately 5/16 inch; and markings are absent.

*Stem.*—Stout; the length is approximately 7/8 inch; and the breadth is approximately 3/32 inch.

*Picking dates.*—Commonly approximately 2 to 4 days earlier than the Tenroy cultivar. During 1990 the dates of first and last pickings of the Obrogala cultivar were August 23rd and September 7th, and the dates of the first and last pickings of the Tenroy cultivar were August, 25th and September 10th. During 1991 the dates of the first and last pickings of the Obrogala cultivar were August 30th and September 13th.

*Calyx.*—Closed. Segments: Broadly lanceolate; approximate; and reflexed from base at apex. Outer surface: Pubescent. Inner surface: Pubescent. Eye: Medium.

*Skin.*—Thin, smooth, glossy and waxed. Dots: Obscure, many relatively even, substantially circular, and pale whitish-yellow in coloration. Ground color: Solid Nopal Red, Plate 1 3 OR blushed uniformly as a solid color covering approximately 90 to 100 percent of the fruit surface when mature on most specimens. The Obrogala cultivar exhibited mature fruit colorimeter values of L=41.2, a=35.05, and b=13.58. This can be compared to mature fruit colorimeter values of L=57.38, a=24.84 and b=20.52 for the Tenroy cultivar. Color markings: Less colored fruit shows hints of indeterminate striping which is considerably less distinct than that of the Tenroy cultivar. Color of markings: Slightly more intense than those of the Tenroy cultivar, Solid Nopal Red, Plate 1 3 OR. Bloom: White with pink fading to white on reverse. General color effect: Color appears approximately 10 days earlier than the Tenroy cultivar, and at maturity covers a greater portion of the fruit skin surface with a deeper, more intense coloration than the Tenroy and Scarlet Gala cultivars. Most fruit shows no striping when mature. Also, the fruit tends to be somewhat more conical in configuration than that of the Tenroy and Scarlet Gala cultivars.

*Flesh.*—Juicy, satiny, and creamy white in appearance. Texture: Firm, tender, fine, and crisp. Flavor: Mild, delicate, and rich. Quality: Best. Starch content: Substantially the same as that of the Tenroy cultivar. However, conversion to sugar is earlier than that of the Tenroy cultivar as indicated by standard starch-iodine test results reported earlier.

*Core.*—Sessile; medium. Bundle area: In longitudinal section it is small and oblate. Bundles: Inconspicuous; in one whorl. Core lines: Clasping; indistinct. Calyx tube: Glabrous toward base; funnel form. Stem of funnel: Long. Depth of tube to shoulder: Approximately 3/16 inch. Entire depth: Approximately 1/2 inch. Styles: Present. Stamens: In one distinct whorl; median. Auxiliary cavity: Present. Seed cells: Axile; open. Cell walls: Thin; approximately 9/16 inch in length; and approximately 3/8 inch in breadh. Longitudinal section: Orbicular; obuse at apex. Surface: Smooth. Cross section: Broad.

*Seeds.*—Length: Approximately 5/16 inch. Breadth: Approximately 3/16 inch. Color: Burnt Umber Plate XXVIII, Color No. 9", tone m.

Use: Market; dessert.

Keeping quality: Good.

Resistance to insects: Good.

Resistance to diseases: Good.

We claim:

1. A new and distinct Gala-type apple tree cultivar having the following combination of chararcteristics:

(a) forms attractive fruit of excellent flavor and texture having a Nopal Red blush over approximately 90 to 100 percent of the skin with hints of striping on less colored fruit and greater red coloration than the Tenroy cultivar, (b) begins color development on the fruit skin approximately 10 days earlier than the Tenroy cultivar, (c) forms fruit which matures for harvest approximately 2 to 4 days earlier than the Tenroy cultivar, (d) forms fruit which tends to be somewhat more conical than that of the Tenroy cultivar, and (e) forms lenticels which tend to be irregularly rounded in the substantial absence of lenticels which are elongated as commonly exhibited by the Tenroy cultivar;

substantially as herein shown and described.

* * * * *